(12) United States Patent
Thornton

(10) Patent No.: US 7,963,284 B2
(45) Date of Patent: Jun. 21, 2011

(54) CUSTOM FITTED MASK AND METHOD OF FORMING SAME

(75) Inventor: W. Keith Thornton, Dallas, TX (US)

(73) Assignee: AirWay Technologies, LLC, Carrollton, TX (US)

( * ) Notice: Subject to any disclaimer, the term of this patent is extended or adjusted under 35 U.S.C. 154(b) by 0 days.

(21) Appl. No.: 10/920,977

(22) Filed: Aug. 18, 2004

(65) Prior Publication Data

US 2005/0016544 A1     Jan. 27, 2005

Related U.S. Application Data

(62) Division of application No. 10/280,803, filed on Oct. 24, 2002, now Pat. No. 6,857,428.

(51) Int. Cl.
*A62B 18/02* (2006.01)
*A62B 18/08* (2006.01)

(52) U.S. Cl. ......... 128/205.25; 128/206.28; 128/206.12; 128/206.14; 128/206.24

(58) Field of Classification Search ............. 128/205.25, 128/206.14, 206.16, 206.21, 206.24, 206.25, 128/206.26, 206.28, 206.29, 207.13, 207.11; 264/222, 219, 220; 425/816, 2
See application file for complete search history.

(56) References Cited

U.S. PATENT DOCUMENTS

| | | | |
|---|---|---|---|
| 339,334 A | 4/1886 | Searle | |
| 690,663 A | 1/1902 | Pratt | |
| 746,869 A | 12/1903 | Moulton | |
| 774,446 A | 11/1904 | Moulton | |
| 781,516 A * | 1/1905 | Guthrie | 128/206.18 |
| 885,196 A | 4/1908 | Steil | |
| 893,213 A * | 7/1908 | Whiteway | 128/206.16 |
| 996,783 A | 7/1911 | Moreau | |
| 1,076,534 A | 10/1913 | Wallen | |
| 1,146,264 A | 7/1915 | Kelly | |
| 1,483,694 A | 2/1924 | Stukey | |
| 1,649,664 A | 11/1927 | Carter | |

(Continued)

FOREIGN PATENT DOCUMENTS

AU     78762/94     9/1994

(Continued)

OTHER PUBLICATIONS

Mayo Clinic Health Letter, vol. 13, No. 7, "Snoring", Jul. 1995.

(Continued)

*Primary Examiner* — Justine R Yu
*Assistant Examiner* — Annette F Dixon
(74) *Attorney, Agent, or Firm* — Baker Botts L.L.P.

(57) ABSTRACT

In one embodiment, a custom-fitted mask includes a thin sheet of deformable material that has been formed and fitted to a portion of a face surrounding the nostrils to conform substantially optimally to unique facial features. The thin sheet includes a perimeter defining only soft cartilaginous portions of the nose and portions on either side of and below the soft cartilaginous portions. and excludes hard bony portions of the nose; and an interior within the perimeter. In another embodiment, a mask blank for using in forming a custom-fitted mask includes a thin sheet of deformable material adapted to be transitioned from a non-deformable state into a deformable state, applied against a portion of a face surrounding the nostrils while the mask blank is in the deformable state, and deformed against the face to cause the mask blank to conform substantially optimally to unique facial features to form the custom-fitted mask.

13 Claims, 6 Drawing Sheets

U.S. PATENT DOCUMENTS

| | | | | |
|---|---|---|---|---|
| 1,674,336 | A | 6/1928 | King | |
| 1,675,202 | A | 6/1928 | Warne | |
| 1,679,748 | A | 8/1928 | Stratton | |
| 2,171,695 | A | 9/1939 | Harper | 32/19 |
| 2,178,128 | A | 10/1939 | Waite | 128/136 |
| 2,383,649 | A | 8/1945 | Heidbrink | 128/142 |
| 2,424,533 | A | 7/1947 | Faires | 128/136 |
| 2,505,028 | A | 4/1950 | Boeger | 128/215 |
| 2,521,039 | A | 9/1950 | Carpenter | 128/136 |
| 2,521,084 | A | 9/1950 | Oberto | 128/141 |
| 2,531,222 | A | 11/1950 | Kesling | 32/14 |
| 2,574,623 | A | 11/1951 | Clyde | 128/136 |
| 2,590,118 | A | 3/1952 | Oddo, Jr. | 128/136 |
| 2,627,268 | A | 2/1953 | Leppich | 128/136 |
| 2,671,446 | A | 3/1954 | Mann | 128/163 |
| 2,712,160 | A | 7/1955 | Sterczek | 18/55.05 |
| 2,833,278 | A | 5/1958 | Ross | 128/136 |
| 2,867,212 | A | 1/1959 | Nunn, Jr. | 128/136 |
| 2,882,893 | A | 4/1959 | Godfroy | 128/136 |
| 2,917,045 | A | 12/1959 | Schildknecht et al. | 128/141 |
| 2,977,636 | A * | 4/1961 | McGuire | 264/154 |
| 3,037,501 | A | 6/1962 | Miller | 128/141 |
| 3,064,354 | A | 11/1962 | Pos | 32/19 |
| 3,107,668 | A | 10/1963 | Thompson | 128/136 |
| 3,124,129 | A | 3/1964 | Grossberg | 128/136 |
| 3,132,647 | A | 5/1964 | Corniello | 128/136 |
| 3,219,033 | A | 11/1965 | Wallshein | 128/136 |
| 3,277,892 | A | 10/1966 | Tepper | 128/172.1 |
| 3,312,216 | A | 4/1967 | Wallshein | 128/136 |
| 3,321,832 | A | 5/1967 | Weisberg | 32/32 |
| 3,330,274 | A | 7/1967 | Bennett | 128/146.7 |
| 3,434,470 | A | 3/1969 | Strickland | 128/136 |
| 3,457,916 | A | 7/1969 | Wolicki | 128/136 |
| 3,513,838 | A | 5/1970 | Foderick et al. | 128/136 |
| 3,522,805 | A | 8/1970 | Wallshein | 128/136 |
| 3,658,058 | A | 4/1972 | Neidhart et al. | 128/147 |
| 3,690,004 | A | 9/1972 | Frush | 32/17 |
| 3,695,265 | A * | 10/1972 | Brevik | 128/206.14 |
| 3,845,768 | A | 11/1974 | Garrahan | |
| 3,854,208 | A | 12/1974 | Arant | 32/19 |
| 3,864,832 | A | 2/1975 | Carlson | 128/136 |
| 3,871,370 | A | 3/1975 | McDonald | 128/136 |
| 3,882,601 | A | 5/1975 | Jahn | 32/17 |
| 3,884,226 | A | 5/1975 | Tepper | 128/136 |
| 4,016,650 | A | 4/1977 | Leusner et al. | 32/17 |
| 4,026,024 | A | 5/1977 | Tradowsky | 32/19 |
| 4,050,457 | A * | 9/1977 | Davidson | 128/202.28 |
| 4,114,614 | A | 9/1978 | Kesling | 128/136 |
| 4,169,473 | A | 10/1979 | Samelson | 128/136 |
| 4,182,312 | A | 1/1980 | Mushabac | 433/68 |
| 4,227,877 | A | 10/1980 | Tureaud et al. | 433/37 |
| 4,233,972 | A | 11/1980 | Hauff et al. | 128/205 |
| 4,240,420 | A * | 12/1980 | Riaboy | 128/206.14 |
| 4,289,127 | A | 9/1981 | Nelson | 128/207.14 |
| 4,294,243 | A * | 10/1981 | Ernsting et al. | 128/201.18 |
| 4,304,227 | A | 12/1981 | Samelson | 128/136 |
| 4,345,592 | A | 8/1982 | Giorgini et al. | 128/204 |
| 4,345,593 | A | 8/1982 | Sullivan | 128/204 |
| 4,354,489 | A * | 10/1982 | Riaboy | 128/206.14 |
| 4,376,628 | A | 3/1983 | Aardse | 433/80 |
| 4,382,783 | A | 5/1983 | Rosenberg | 433/19 |
| 4,392,490 | A | 7/1983 | Mattingly et al. | 128/202 |
| 4,397,701 | A | 8/1983 | Johnson et al. | 156/62 |
| 4,433,956 | A | 2/1984 | Witzig | 433/7 |
| 4,439,147 | A | 3/1984 | Magill et al. | 433/3 |
| 4,439,149 | A | 3/1984 | Devincenzo | 433/6 |
| 4,454,090 | A | 6/1984 | Saumell | 264/154 |
| 4,454,880 | A * | 6/1984 | Muto et al. | 128/205.25 |
| 4,470,413 | A | 9/1984 | Warncke | 128/201.18 |
| 4,495,945 | A | 1/1985 | Liegner | 128/200.26 |
| 4,505,672 | A | 3/1985 | Kurz | 433/6 |
| 4,530,662 | A | 7/1985 | Andersson et al. | 433/37 |
| 4,553,549 | A | 11/1985 | Pope et al. | 128/421 |
| 4,568,280 | A | 2/1986 | Ahlin | 433/6 |
| 4,569,342 | A | 2/1986 | von Nostitz | 128/136 |
| 4,593,686 | A | 6/1986 | Lloyd et al. | 128/136 |
| 4,602,905 | A | 7/1986 | O'Keefe, III | 433/41 |
| 4,639,220 | A | 1/1987 | Nara et al. | 433/69 |
| 4,655,213 | A | 4/1987 | Rapoport et al. | 128/205.25 |
| 4,668,188 | A | 5/1987 | Wolfenson et al. | 433/37 |
| 4,669,459 | A | 6/1987 | Spiewak et al. | 128/136 |
| 4,676,240 | A | 6/1987 | Gardy | 128/207.14 |
| 4,706,683 | A | 11/1987 | Chilton et al. | 128/654 |
| 4,715,368 | A | 12/1987 | George | 128/136 |
| 4,721,465 | A * | 1/1988 | Barasz | 433/137 |
| 4,773,853 | A | 9/1988 | Kussick | 433/6 |
| 4,784,123 | A | 11/1988 | Robeson | 128/90 |
| 4,799,500 | A | 1/1989 | Newbury | 128/859 |
| 4,856,509 | A * | 8/1989 | Lemelson | 128/206.19 |
| 4,858,605 | A * | 8/1989 | Levy | 128/203.11 |
| 4,858,606 | A | 8/1989 | Hamlin | 128/204 |
| 4,862,903 | A | 9/1989 | Campbell | 128/861 |
| 4,870,962 | A | 10/1989 | Sitnik | 128/205 |
| 4,886,056 | A | 12/1989 | Simpson | 128/201 |
| 4,892,478 | A | 1/1990 | Tateosian et al. | 433/6 |
| 4,901,737 | A | 2/1990 | Toone | 128/848 |
| 4,906,234 | A | 3/1990 | Voychehovski | 604/79 |
| 4,919,128 | A | 4/1990 | Kopala et al. | 128/207.18 |
| 4,932,867 | A | 6/1990 | Ueno | 433/69 |
| 4,941,212 | A | 7/1990 | Liff | 2/206 |
| 4,955,393 | A | 9/1990 | Adell | 128/859 |
| 4,957,124 | A | 9/1990 | Mooney | 132/200 |
| RE33,442 | E | 11/1990 | George | 128/860 |
| 5,003,633 | A | 4/1991 | Itoh | 2/9 |
| 5,003,994 | A | 4/1991 | Cook | 128/848 |
| 5,011,407 | A | 4/1991 | Pelerin | 433/48 |
| 5,018,533 | A | 5/1991 | Hawkins | 128/848 |
| 5,026,278 | A | 6/1991 | Oxman et al. | 433/41 |
| 5,028,232 | A | 7/1991 | Snow | 433/24 |
| 5,040,976 | A | 8/1991 | Ubel, III et al. | 433/41 |
| 5,042,478 | A | 8/1991 | Kopala et al. | 128/207.18 |
| 5,042,506 | A | 8/1991 | Liberati | 128/848 |
| 5,046,512 | A | 9/1991 | Murchie | 128/848 |
| 5,052,409 | A | 10/1991 | Tepper | 128/859 |
| 5,055,039 | A | 10/1991 | Abbatte et al. | 433/24 |
| 5,056,534 | A | 10/1991 | Wright | 128/848 |
| 5,062,421 | A | 11/1991 | Burns et al. | 128/205.27 |
| 5,064,371 | A | 11/1991 | Smeltzer | 433/37 |
| 5,065,756 | A | 11/1991 | Rapoport | 128/204 |
| 5,066,231 | A | 11/1991 | Oxman et al. | 433/214 |
| 5,078,600 | A | 1/1992 | Austin | 433/73 |
| 5,092,346 | A | 3/1992 | Hays et al. | 128/848 |
| 5,103,838 | A | 4/1992 | Yousif | 128/859 |
| 5,112,225 | A | 5/1992 | Diesso | 433/48 |
| 5,117,816 | A | 6/1992 | Shapiro et al. | 128/200.24 |
| 5,154,184 | A | 10/1992 | Alvarez | 128/848 |
| 5,154,609 | A | 10/1992 | George | 433/68 |
| 5,183,057 | A | 2/1993 | Syrop et al. | 128/845 |
| 5,188,529 | A | 2/1993 | Lüth | 433/68 |
| 5,190,457 | A | 3/1993 | Schreinemakers | 433/214 |
| 5,193,532 | A | 3/1993 | Moa et al. | 128/204 |
| 5,213,498 | A | 5/1993 | Pelerin | 433/37 |
| 5,233,978 | A * | 8/1993 | Callaway | 128/205.25 |
| 5,243,971 | A | 9/1993 | Sullivan et al. | 128/205 |
| 5,245,995 | A | 9/1993 | Sullivan et al. | 128/204 |
| 5,267,557 | A | 12/1993 | Her-Mou | 128/206.21 |
| 5,267,862 | A | 12/1993 | Parker | 433/215 |
| 5,277,202 | A | 1/1994 | Hays | 128/848 |
| 5,280,305 | A * | 1/1994 | Monroe et al. | 347/129 |
| 5,284,161 | A | 2/1994 | Karell | 128/848 |
| 5,313,960 | A | 5/1994 | Tomasi | 128/848 |
| 5,316,020 | A | 5/1994 | Truffer | 128/848 |
| 5,320,533 | A | 6/1994 | Lee | 433/218 |
| 5,365,945 | A | 11/1994 | Halstrom | 128/848 |
| 5,370,533 | A | 12/1994 | Bushnell | 433/36 |
| 5,373,859 | A | 12/1994 | Forney | 128/846 |
| 5,392,773 | A | 2/1995 | Bertrand | 128/206.11 |
| 5,409,017 | A | 4/1995 | Lowe | 128/848 |
| 5,415,544 | A | 5/1995 | Oxman et al. | 433/48 |
| 5,427,117 | A | 6/1995 | Thornton | 128/848 |
| 5,456,264 | A | 10/1995 | Series et al. | 128/725 |
| 5,458,137 | A | 10/1995 | Axe et al. | 128/204 |
| 5,477,850 | A | 12/1995 | Zegler et al. | 128/202 |
| 5,488,944 | A * | 2/1996 | Kennedy | 128/202.18 |
| 5,503,146 | A | 4/1996 | Froehlich et al. | 128/204 |
| 5,503,167 | A * | 4/1996 | Wilson et al. | 132/319 |
| 5,503,552 | A | 4/1996 | Diesso | 433/37 |

| | | | |
|---|---|---|---|
| 5,517,983 A | 5/1996 | Deighan et al. | 128/204 |
| 5,537,994 A | 7/1996 | Thornton | 128/205 |
| 5,537,999 A | 7/1996 | Dearman et al. | 128/205 |
| 5,538,000 A | 7/1996 | Rudolph | 128/205 |
| 5,538,014 A * | 7/1996 | Wilson et al. | 128/863 |
| 5,540,223 A * | 7/1996 | Starr et al. | 128/205.25 |
| 5,551,419 A | 9/1996 | Froehlich et al. | 128/204 |
| 5,551,872 A | 9/1996 | Mena | 433/37 |
| 5,558,090 A | 9/1996 | James | 128/207.18 |
| RE35,339 E | 10/1996 | Rapoport | 128/204 |
| 5,560,354 A | 10/1996 | Berthon-Jones et al. | 128/205 |
| 5,562,449 A | 10/1996 | Jacobs et al. | 433/215 |
| 5,566,683 A | 10/1996 | Thornton | 128/848 |
| 5,582,517 A | 12/1996 | Adell | 433/6 |
| 5,592,935 A | 1/1997 | Elstran et al. | 128/205 |
| 5,611,485 A | 3/1997 | Davis | 239/8 |
| 5,657,751 A | 8/1997 | Karr, Jr. | 128/205 |
| 5,657,752 A | 8/1997 | Landis et al. | 128/207 |
| 5,662,101 A | 9/1997 | Ogden et al. | 128/205.25 |
| 5,676,133 A | 10/1997 | Hickle et al. | 128/205 |
| 5,678,567 A | 10/1997 | Thornton et al. | 128/848 |
| 5,687,715 A | 11/1997 | Landis et al. | 128/207.18 |
| 5,713,349 A | 2/1998 | Keaney | 128/204 |
| 5,718,244 A | 2/1998 | Thornton | 128/864 |
| 5,718,500 A | 2/1998 | Vinci Guerra et al. | 2/431 |
| 5,720,280 A | 2/1998 | Elstran et al. | 128/205 |
| 5,720,302 A | 2/1998 | Belfer | 128/201.26 |
| 5,724,965 A * | 3/1998 | Handke et al. | 128/207.13 |
| 5,727,544 A * | 3/1998 | Miura | 128/201.13 |
| 5,746,201 A | 5/1998 | Kidd | 128/206 |
| 5,752,510 A | 5/1998 | Goldstein | 128/207 |
| 5,755,219 A | 5/1998 | Thornton | 128/201 |
| 5,807,100 A | 9/1998 | Thornton | 433/48 |
| 5,810,749 A | 9/1998 | Maas | 602/6 |
| 5,829,441 A | 11/1998 | Kidd et al. | 128/848 |
| 5,832,918 A | 11/1998 | Pantino | 128/205.25 |
| 5,846,082 A * | 12/1998 | Thornton | 433/215 |
| 5,887,587 A | 3/1999 | Groenke | 128/207 |
| 5,891,372 A | 4/1999 | Besset et al. | 264/46.5 |
| 5,954,048 A | 9/1999 | Thornton | 128/201 |
| 5,983,892 A | 11/1999 | Thornton | 128/201 |
| 5,988,166 A | 11/1999 | Hayek | 128/205 |
| 6,012,455 A * | 1/2000 | Goldstein | 128/207.18 |
| 6,083,442 A | 7/2000 | Gabilly | 264/163 |
| 6,092,521 A * | 7/2000 | Miura | 128/201.13 |
| 6,119,694 A * | 9/2000 | Correa et al. | 128/207.13 |
| 6,123,071 A | 9/2000 | Berthon-Jones et al. | 128/204.18 |
| 6,155,262 A | 12/2000 | Thornton et al. | 128/859 |
| 6,155,267 A | 12/2000 | Thornton | 128/859 |
| 6,209,542 B1 | 4/2001 | Thornton | 128/206.29 |
| 6,247,926 B1 | 6/2001 | Thornton | 433/48 |
| 6,263,871 B1 | 7/2001 | Brown et al. | 128/200.29 |
| D448,473 S | 9/2001 | Barnett et al. | D24/110.1 |
| 6,305,376 B1 | 10/2001 | Thornton | 128/848 |
| 6,325,064 B1 | 12/2001 | Thornton | 128/204.18 |
| 6,374,824 B1 | 4/2002 | Thornton | 128/201.26 |
| 6,405,729 B1 * | 6/2002 | Thornton | 128/848 |
| 6,412,488 B1 | 7/2002 | Barnett et al. | 128/207.13 |
| 6,464,924 B1 | 10/2002 | Thornton | 264/331.12 |
| 6,494,206 B1 * | 12/2002 | Bergamaschi et al. | 128/206.24 |
| 6,516,805 B1 | 2/2003 | Thornton | 128/848 |
| 6,571,798 B1 | 6/2003 | Thornton | 128/206.21 |
| 6,645,413 B2 | 11/2003 | Jacobs | 264/222 |
| 6,675,802 B1 | 1/2004 | Thornton | 128/206.29 |
| 6,877,513 B2 | 4/2005 | Scarberry et al. | 128/848 |
| 7,077,138 B2 * | 7/2006 | Bateman et al. | 128/206.14 |
| 2002/0000230 A1 | 1/2002 | Gaskell | 128/848 |
| 2002/0129818 A1 | 9/2002 | Morgan et al. | 128/206.26 |
| 2004/0237965 A1 | 12/2004 | Bibi et al. | 128/206.29 |
| 2006/0005837 A1 | 1/2006 | Thornton | 128/205.25 |
| 2006/0124131 A1 | 6/2006 | Chandran et al. | 128/206.28 |

FOREIGN PATENT DOCUMENTS

| | | |
|---|---|---|
| AU | 27647/95 | 6/1995 |
| DE | 156627 | 12/1904 |
| DE | 2320501 | 11/1974 |
| DE | 3543931 | 6/1987 |
| DE | 3707952 | 9/1988 |
| DE | 3719009 | 12/1988 |
| DE | 44 38 512 A1 | 10/1994 |
| DE | 29506512 | 7/1995 |
| DE | 19524534 | 5/1996 |
| DE | 198 46 686 A1 | 10/1998 |
| EP | 0312368 | 4/1989 |
| EP | 0359135 | 3/1990 |
| FR | 2658725 | 2/1990 |
| FR | 2 731 624 A1 | 3/1995 |
| FR | 2731624 | 9/1996 |
| GB | 1569129 | 6/1980 |
| WO | WO91/12777 | 9/1991 |
| WO | WO98/20924 | 5/1998 |
| WO | WO98/26736 | 6/1998 |
| WO | WO98/46177 | 10/1998 |
| WO | WO 98/46177 | 10/1998 |

OTHER PUBLICATIONS

Photocopies of 2-piece dental device manufactured by Currie-Gibson Dental Laboratory, Inc. prior to Apr. 13, 1993.

Farrar & McCarthy, "A Clinical Outline of Temporomandibular Joint Diagnosis and Treatment," Normandie Study Group for TMJ Dysfunction, 3 pages, 1983.

Professional Positioners brochure, "Dedicated to Excellence," 4 pages.

Schmidt-Nowara, et al., "Oral Appliances for the Treatment of Snoring and Obstructive Sleep Apnea: A Review," Sleep, 18(6):501-510, 1995.

George, "Treatment of Snoring and Obstructive Sleep Apnea with a Dental Device," General Dentistry, 5 pages, Jul.-Aug. 1993.

Database WOI, Section PQ, Week 9039, Derwent Publications, Ltd., London, GB XP-002116355—Abstract "Surgical Mouth Air Duct", Dec. 15, 1989.

PCT International Search Report, PCT/US97/08708, 4 pages, Aug. 12, 1997.

PCT, International Searching Authority, PCT/US03/13705, 5 page, Oct. 10, 2003.

W. Keith Thornton, "Device and Mask for Improving a User's Breathing," U.S. Appl. No. 10/428,904, pending (019651.0225), May 1, 2003.

W. Keith Thornton, "Custom Fitted Mask and Method of Forming Same," U.S. Appl. No. 10/280,803, pending (019651.0228), Oct. 24, 2002.

W. Keith Thornton, "Custom Fitted Mask Configured for Coupling to an External Gas Supply System and Method of forming Same," U.S. Appl. No. 10/890,547, pending, Jul. 12, 2004.

"Donning the Mask," Dräger. X-plore 5500.2006.Dräger Safety, http://www.draeger-usa.com/ST/internet/pdf/US/protection/AnlegiPO_X-plore_5500_US.pdf, 2 pages.

Thornton, "Multi-Chamber Mask and Method of Forming the Same," U.S. Appl. No. 11/428,933, 23 pages.

PCT, Notification of Transmittal of the International Search Report and the Written Opinion of the International Searching Authority, or the Declaration, PCT/US06/26622, 11 pages, Feb. 21, 2007.

European Patent Office, Supplementary European Search Report, Application No. EP 03 80 9555, Mar. 27, 2009, 3 pages.

European Patent Office Communication, Application No. 03 809 555.0-1257, Applicant: W. Keith Thornton, 4 pages, dated Aug. 7, 2009.

Canadian Intellectual Property Office, Application No. 2,502,280, Applicant: W. Keith Thornton, 3 pages, dated Feb. 23, 2010.

Canadian Intellectual Property Office; Office Action; application No. 2,502,280; 3 pages, Jan. 4, 2011.

* cited by examiner

CUSTOM FITTED MASK AND METHOD OF FORMING SAME

RELATED APPLICATION

This application is a divisional application of U.S. application Ser. No. 10/280,803, filed Oct. 24, 2002 and entitled "Custom Fitted Mask and Method of Forming Same," now U.S. Pat. No. 6,857,428.

TECHNICAL FIELD

This invention relates generally to masks for use in medical or other clinical applications, and more particularly to a custom fitted mask and method of forming same.

BACKGROUND

Many people experience breathing problems on a recurring basis, which often results in sleep disordered breathing (i.e. difficulty sleeping, snoring, or other more serious conditions such as obstructive sleep apnea). As technology advances, people with such breathing problems demand increased performance and comfort. Previous devices for improving a user's breathing have included custom fitted masks that help deliver air or another suitable gas to the user's nose at positive pressure to help force open the user's breathing passage and thus improve the user's breathing. However, previous masks may be relatively expensive due to the expertise often required to design, manufacture, and fit the masks to each particular user. Furthermore, previous masks have often been fitted to the user's unique bone structure and facial features rather poorly, if at all. As a result, previous masks have often failed to adequately prevent leakage from around the perimeter of the mask, have caused discomfort for users, and have been relatively ineffective in treating breathing problems such as sleep disordered breathing.

SUMMARY OF THE INVENTION

According to the present invention, problems and disadvantages associated with previous custom fitted masks and methods for forming them may be reduced or eliminated.

According to one embodiment, a custom fitted mask includes a thin sheet of deformable material that has been formed and fitted to a portion of a user's face surrounding the user's nostrils to conform substantially optimally to the user's unique facial features. The portion of the user's face includes only soft cartilaginous portions of the user's nose and portions of the user's face on either side of and below the soft cartilaginous portions of the user's nose. The portion of the user's face excludes hard bony portions of the user's nose generally above the soft cartilaginous portions of the user's nose.

According to another embodiment, a mask blank for using in forming a custom fitted mask includes a thin sheet of deformable material adapted to be transitioned from a nondeformable state into a deformable state, applied against at least a portion of a user's face surrounding the user's nostrils while the mask blank is in the deformable state, and deformed against the portion of the user's face to cause the mask blank to conform substantially optimally to the user's unique facial features to form the custom fitted mask.

Certain embodiments of the present invention may provide one or more technical advantages. For example, in certain embodiments, a custom fitted mask may be formed and fitted to a particular user relatively quickly and easily, with little expertise required on the part of the clinical professional who is forming and fitting the mask, typically resulting in improved efficiency for the clinical professional and reduced cost to the user. Also in contrast to prior masks, in certain embodiments, a custom fitted mask may be formed and fitted to a particular user so as to conform substantially optimally to the user's unique facial structure and features. As a result, the custom fitted mask of the present invention may provide improved fit, reduced leakage, increased comfort, and better performance, whether in treating breathing problems such as sleep disordered breathing or for any other suitable purpose for which the custom fitted mask is used. Certain embodiments of the present invention may provide some, all, or more of these advantages. Certain embodiments may provide one or more other advantages, one or more of which may be readily apparent to those skilled in the art based on the figures, descriptions, and claims included herein.

BRIEF DESCRIPTION OF THE DRAWINGS

For a more complete understanding of the present invention and advantages thereof, reference is made to the following descriptions taken in conjunction with the accompanying drawings, in which like reference numbers indicate like features and wherein.

DESCRIPTION OF EXAMPLE EMBODIMENTS

Figure 1:
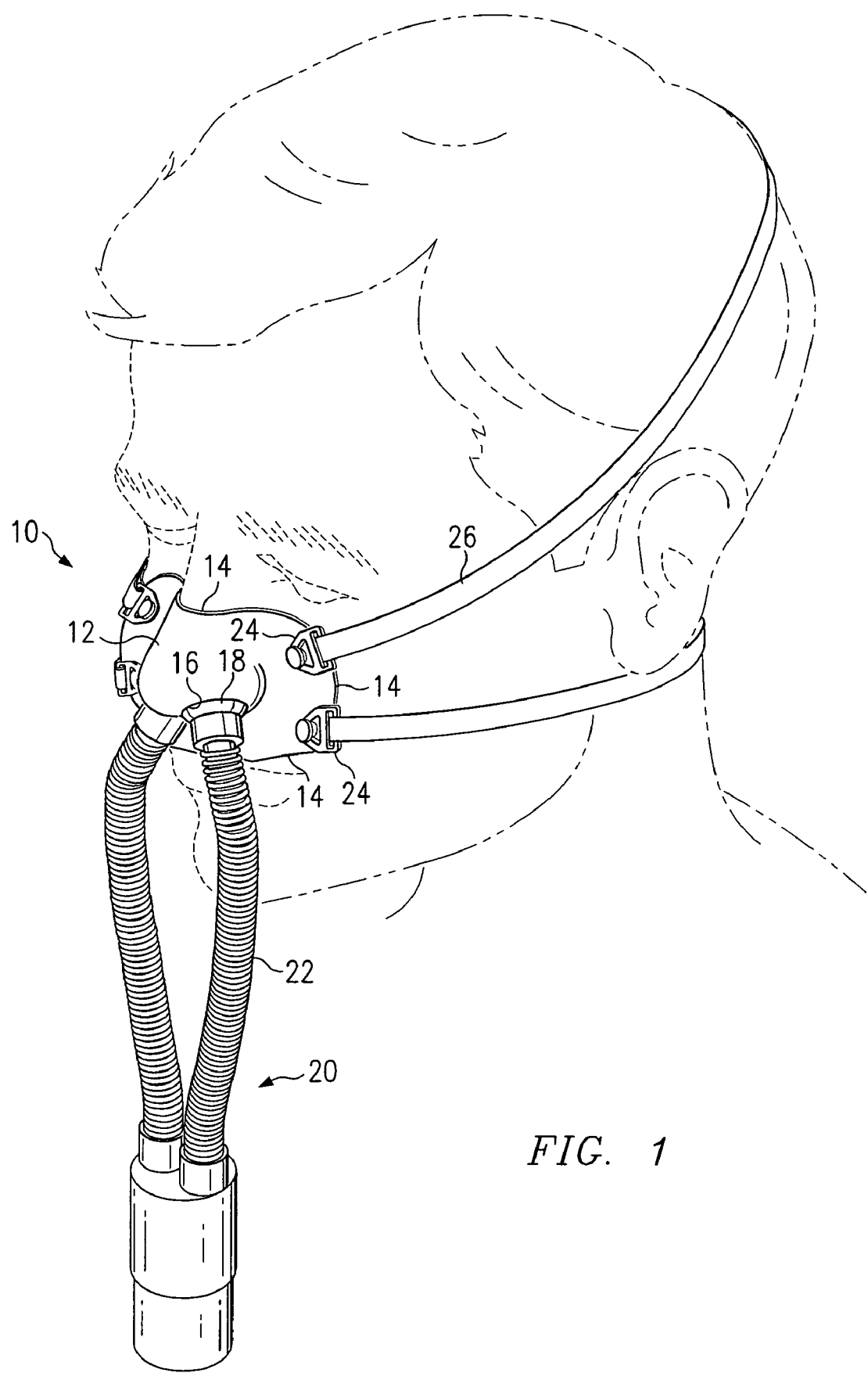
FIG. 1 illustrates an example system for improving a user's breathing including a custom fitted mask.

FIG. 1 illustrates an example system 10 for improving a user's breathing including an example custom fitted mask 12. Mask 12 includes a perimeter 14 and holes 16, one for each of the user's nostrils, into which fittings 18 may be inserted during or after formation and fitting of mask 12. Fittings 18 may be used to couple mask 12 to an external system 20, such as a continuous positive air pressure (CPAP) system, for supplying air or another gas to the user's nose at positive pressure to help open the user's breathing passage and thereby improve the user's breathing. For example, system 10 may include tubes 22 that snap onto, are force fitted onto, or otherwise couple to fittings 18. Mask 12 may include buckles or other devices 24 to couple mask 12 to one or more straps 26, which may help secure mask 12 to the user's face during use. Devices 24 may be coupled to mask 12 during or after formation and fitting of mask 12. Although straps 26 are described as an example, mask 12 being secured in any appropriate manner.

Figure 2:
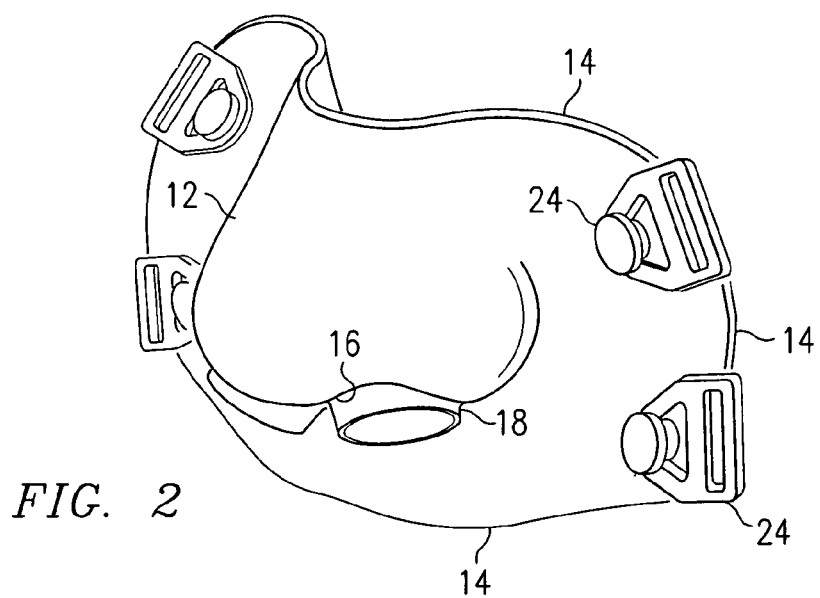
FIG. 2 illustrates a larger view of an example custom fitted mask.
Figure 3:
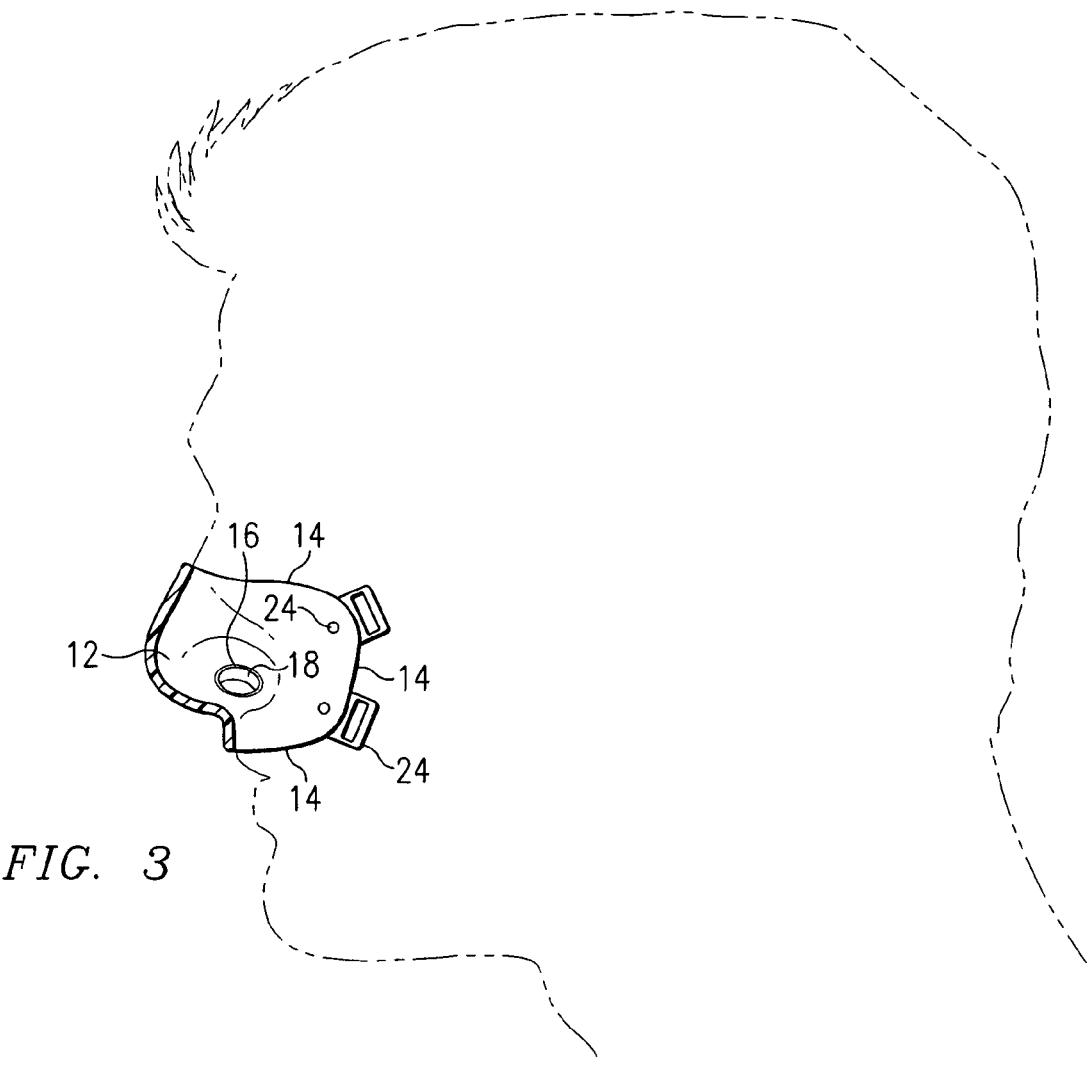
FIG. 3 illustrates an interior view of an example custom fitted mask.

Mask 12 is preferably formed and fitted to the user's face so as to conform substantially optimally to the user's unique bone structure and facial features, including at least a portion of the user's nose surrounding the user's nostrils. In one embodiment, mask 12 covers only the soft cartilaginous portions of the user's nose and portions of the user's face to the sides of and below the soft cartilaginous portions of the user's nose, but does not cover the hard bony portions of the user's nose generally above the soft cartilaginous portions of the user's nose. This may allow custom fitted mask 12 to better conform to the unique shape of the user's face and, as a result of the improved fit, to provide reduced leakage, increased comfort, and better performance. FIG. 2 illustrates a larger view of an example mask 12, while FIG. 3 illustrates an interior view of an example mask 12.

Figures 4A, 4B:
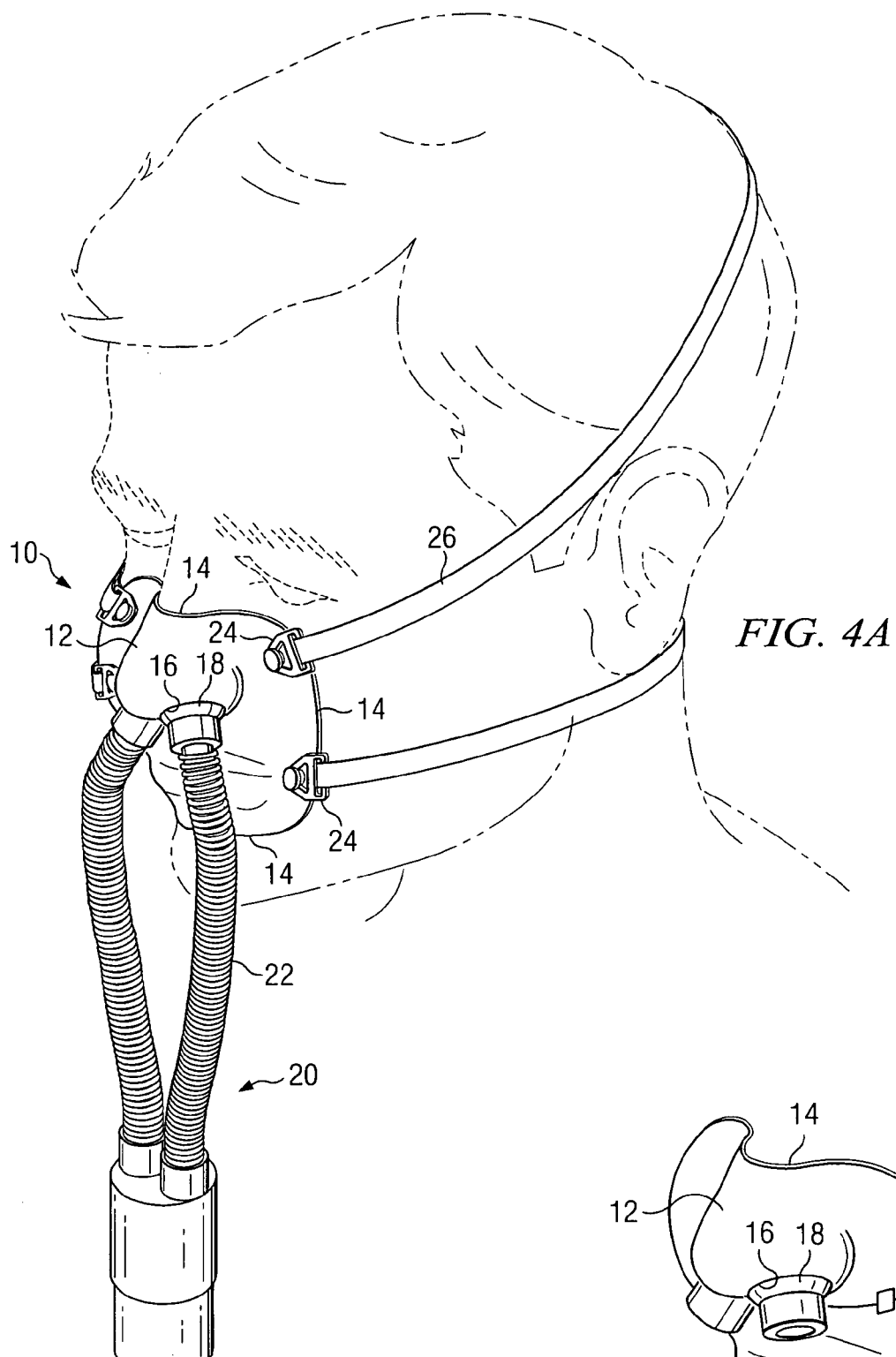
FIGS. 4A and 4B illustrate example custom fitted masks covering a portion of the user's nose and the user's mouth.

In another embodiment, as illustrated in FIGS. 4A and 4B, mask 12 covers at least a portion of the user's nose surrounding the user's nostrils (which may or may not be limited to the soft cartilaginous portions of the user's nose and portions of the user's face to the sides of and below the soft cartilaginous portions of the user's nose) and additionally covers the user's mouth to prevent leakage from the user's mouth. Such a mask 12 may be formed from a single sheet of deformable material or may be formed from multiple sheets of deformable material (e.g., a first covering the user's nose and a second covering the user's mouth) coupled to one another using one or more screws, clips, glue, the same or a different deformable material that is chemically bonded to the sheets of deformable material, or another appropriate fastening technique. Where multiple sheets of deformable material are used, the multiple sheets may be customized for the user at the same or at different times. For example, a first sheet may be customized to cover at least a portion of the user's nose at a first time and, if appropriate, a second sheet may be customized to cover the user's mouth at a subsequent second time and then coupled to the first sheet.

Figure 5A:
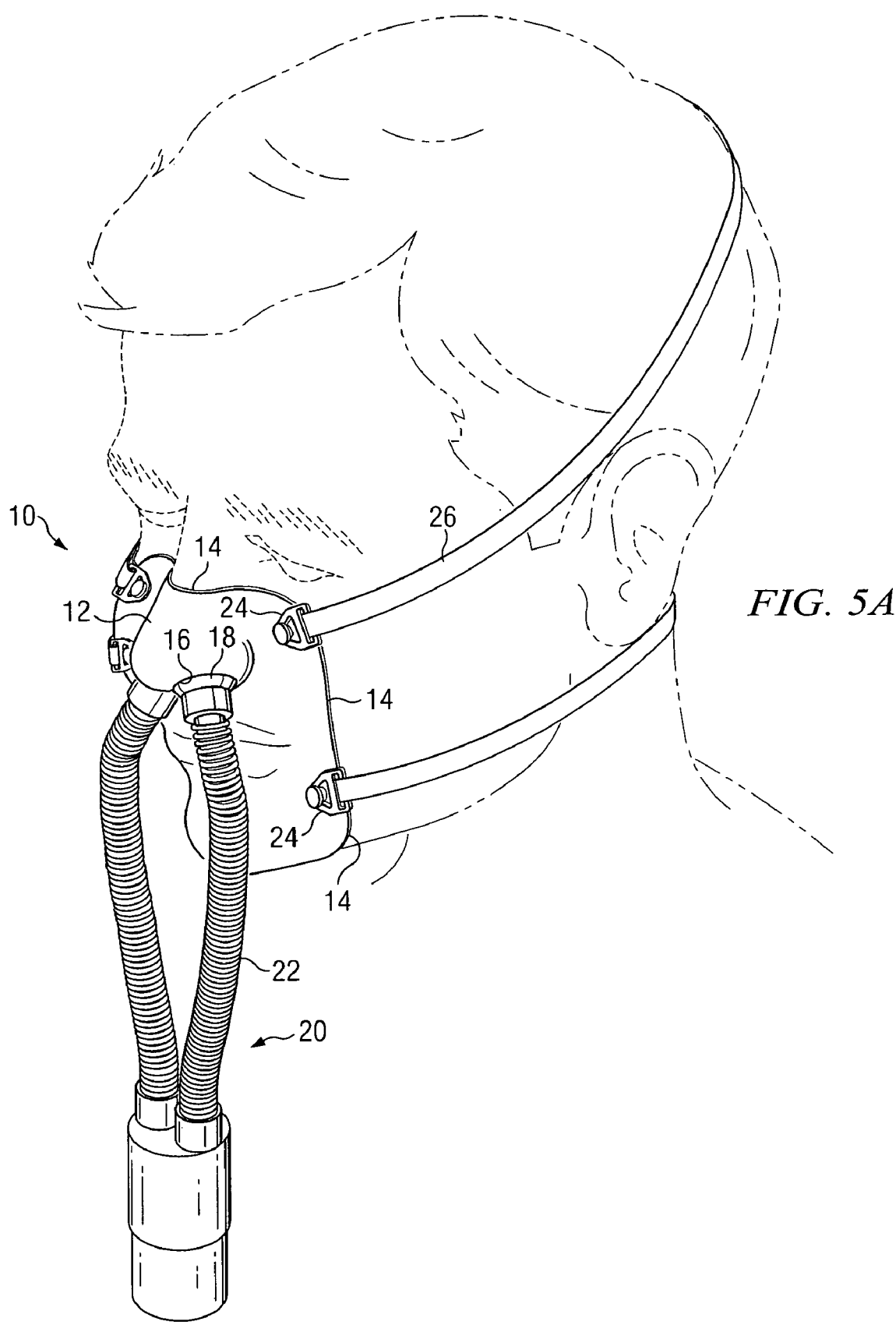
FIGS. 5A, 5B, and 5C illustrate example custom fitted masks covering a portion of the user's nose, the user's mouth, and the user's chin.
Figure 5B:
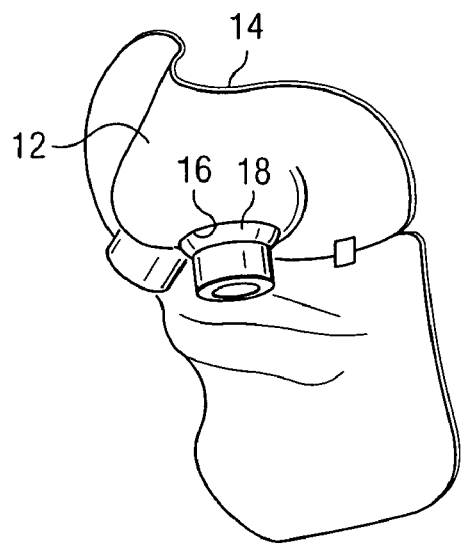
Figure 5C:
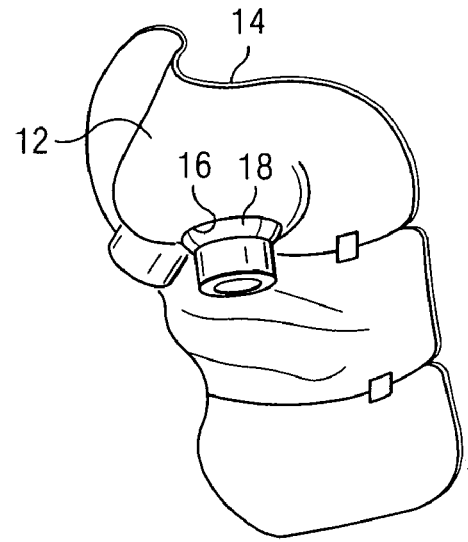

In another embodiment, as illustrated in FIGS. 5A, 5B, and 5C, mask 12 covers at least a portion of the user's nose surrounding the user's nostrils (which may or may not be limited to the soft cartilaginous portions of the user's nose and portions of the user's face to the sides of and below the soft cartilaginous portions of the user's nose), covers the user's mouth, and additionally covers at least a portion of the user's face below the user's chin to better secure mask 12 to the user's face. Such a mask 12 may be formed from a single sheet of deformable material or may be formed from multiple sheets of deformable material (e.g., a first covering the user's nose and a second covering the user's mouth and chin or a first covering the user's nose, a second covering the user's mouth, and a third covering the user's chin) coupled to one another using one or more screws, clips, glue, the same or a different deformable material that is chemically bonded to the sheets of deformable material, or another appropriate fastening technique. Where multiple sheets of deformable material are used, the multiple sheets may be customized for the user at the same or at different times. For example, a first sheet may be customized to cover at least a portion of the user's nose at a first time and, if appropriate, a second sheet may be customized to cover the user's mouth and chin at a subsequent second time and then coupled to the first sheet.

In one embodiment, mask 12 begins as a deformable mask blank made of a suitable deformable material. For example, a mask blank may include a suitable thermoplastic polymer and suitable fillers, stabilizers, coloring agents, antioxidants, antimicrobial agents, or other materials. As another example, a mask blank may include a light curing material such as the material sold under the name TRIAD by DENTSPLY INTERNATIONAL INC. Such materials are well known in various contexts to those skilled in the art.

In a more particular embodiment, a mask blank may include, possibly in addition to one or more other materials, one or more of the polycaprolactone polymers or other aliphatic polyesters that are described in U.S. Pat. Nos. 4,784,123 and 5,112,225 and product literature of UNION CARBIDE CORPORATION. One or more polycaprolactone polymers may have the formula:

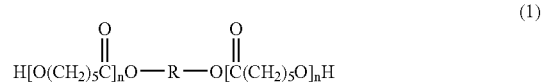

(1)

where R is an aliphatic hydrocarbon and n may range between approximately 300 to approximately 650. The TONE polycaprolactone polymers are described in U.S. Pat. Nos. 4,784,123 and 5,112,225 and product literature of UNION CARBIDE CORPORATION as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

(2)

where R is an aliphatic hydrocarbon. Where a mask blank includes one or more polycaprolactone polymers, any suitable polycaprolactone polymer or polymers may be used. In general, polycaprolactone polymers may display desirable dimensional stability and thermoplasticity during cooling, biocompatibility, and a variety of other characteristics making them suitable for use in forming the mask blanks described herein.

In one embodiment, a mask blank may include a thin sheet of deformable material that is already contoured in the shape of a portion of a generic user's face, including at least the portion of the generic user's nose surrounding the generic user's nostrils. For example, the mask blank may be sized and shaped such that it will cover only the soft cartilaginous portions of the generic user's nose and portions of the generic user's face to the sides of and below the soft cartilaginous portions of the generic user's nose, but will not cover the hard bony-portions of the generic user's nose generally above the soft cartilaginous portions of the generic user's nose. In another embodiment, a mask blank may include a thin sheet of deformable material that is substantially flat except for a depression sufficient to accommodate a generic user's nose, including at least the portion of the generic user's nose surrounding the user's nostrils. In another embodiment, a mask blank may include a thin sheet of deformable material that is substantially flat over its entire surface and does not include any depressions. Thin sheets of an appropriate deformable material may be obtained, for example, from CHESAPEAKE MEDICAL PRODUCTS, INC. In all cases, a mask blank may include pre-formed holes positioned according to the position of a generic user's nostrils. Mask blanks may be formed using an injection molding process (i.e. deformable material is placed into an injection molding machine while in a liquid state), using a pressing process (i.e. deformable material is placed into a press while in a deformable state), or using any other suitable technique. Mask blanks may be sized for various classes of generic users, for example, large for men, medium for women, and small for children. In one embodiment, mask blanks may be mass produced quickly, inexpensively, and with high quality and uniformity. Mask blanks may include fittings 18, devices 24, or any other suitable features.

To form and fit mask 12 for a particular user using the mask blank, the mask blank is placed in a deformable state. For example, where the deformable material of the mask blank includes one or more polycaprolactone polymers, the mask blank may be heated in a microwave oven, in water or other non-solvent neutral liquid, or in any other suitable manner to between approximately 140° F. and approximately 180° F. so as to place the mask blank in a deformable state. If desired, features such as fittings 18 and devices 24 may be coupled to the mask blank at this time if such features are not already coupled to the mask blank. The deformable material may chemically bond to features such as fittings 18 and devices 24 while the mask blank is in a deformable state to produce an integral unit. While in a deformable state, the mask blank is brought in contact with the user's face, including at least a portion of the user's nose surrounding the user's nostrils. The mask blank is then pressed against or otherwise allowed to conform to the user's unique bone structure and facial features to form mask 12. As the deformable material cools and hardens, mask 12 solidifies and will retain its custom fitted shape. Before or after the deformable material solidifies into its final custom fitted shape, mask 12 is removed from the user's face and is ready for use, for example, in treating sleep disordered breathing.

As described above, mask 12 is preferably formed and fitted to the user's face so as to conform substantially optimally to the user's unique bone structure and facial features, including at least a portion of the user's nose surrounding the user's nostrils. In one embodiment, mask 12 covers only the soft cartilaginous portions of the user's nose and portions of the user's face to the sides of and below the soft cartilaginous portions of the user's nose, but does not cover the hard bony portions of the user's nose generally above the soft cartilaginous portions of the user's nose. This may allow custom fitted mask 12 to better conform to the unique shape of the user's face and, as a result of the improved fit, to provide reduced leakage, increased comfort, and better performance. In another embodiment, mask 12 covers at least a portion of the user's nose surrounding the user's nostrils (which may or may not be limited to the soft cartilaginous portions of the user's nose and portions of the user's face to the sides of and below the soft cartilaginous portions of the user's nose) and additionally covers the user's mouth to prevent leakage from the user's mouth. In another embodiment, mask 12 covers at least a portion of the user's nose surrounding the user's nostrils (which may or may not be limited to the soft cartilaginous portions of the user's nose and portions of the user's face to the sides of and below the soft cartilaginous portions of the user's nose), covers the user's mouth, and additionally covers at least a portion of the user's face below the user's chin to better secure mask 12 to the user's face.

Figure 6A:
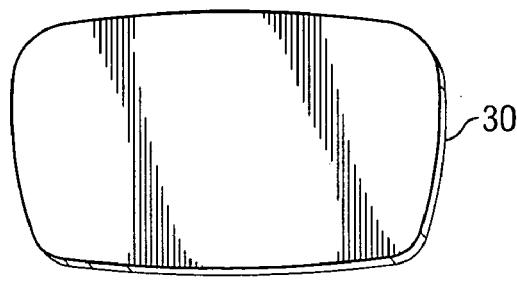
FIGS. 6A, 6B, and 6C illustrate example mask blanks.
Figure 6B:
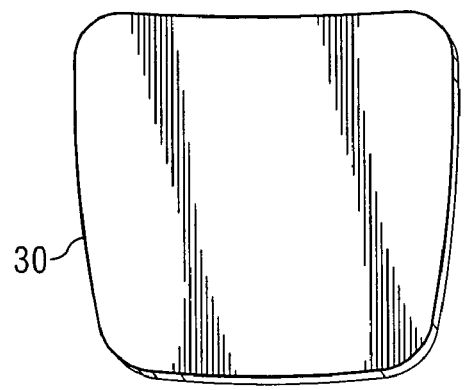
Figure 6C:
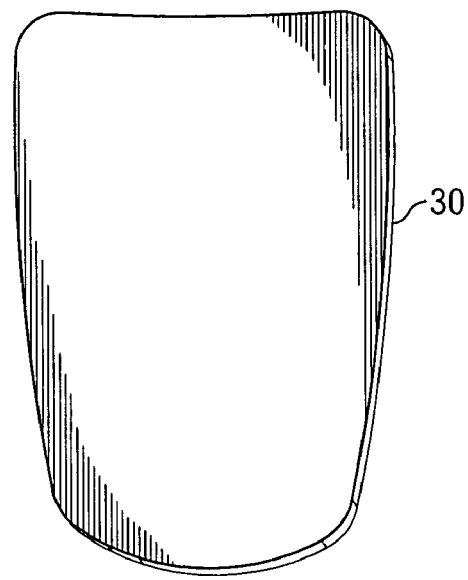
Figure 7:
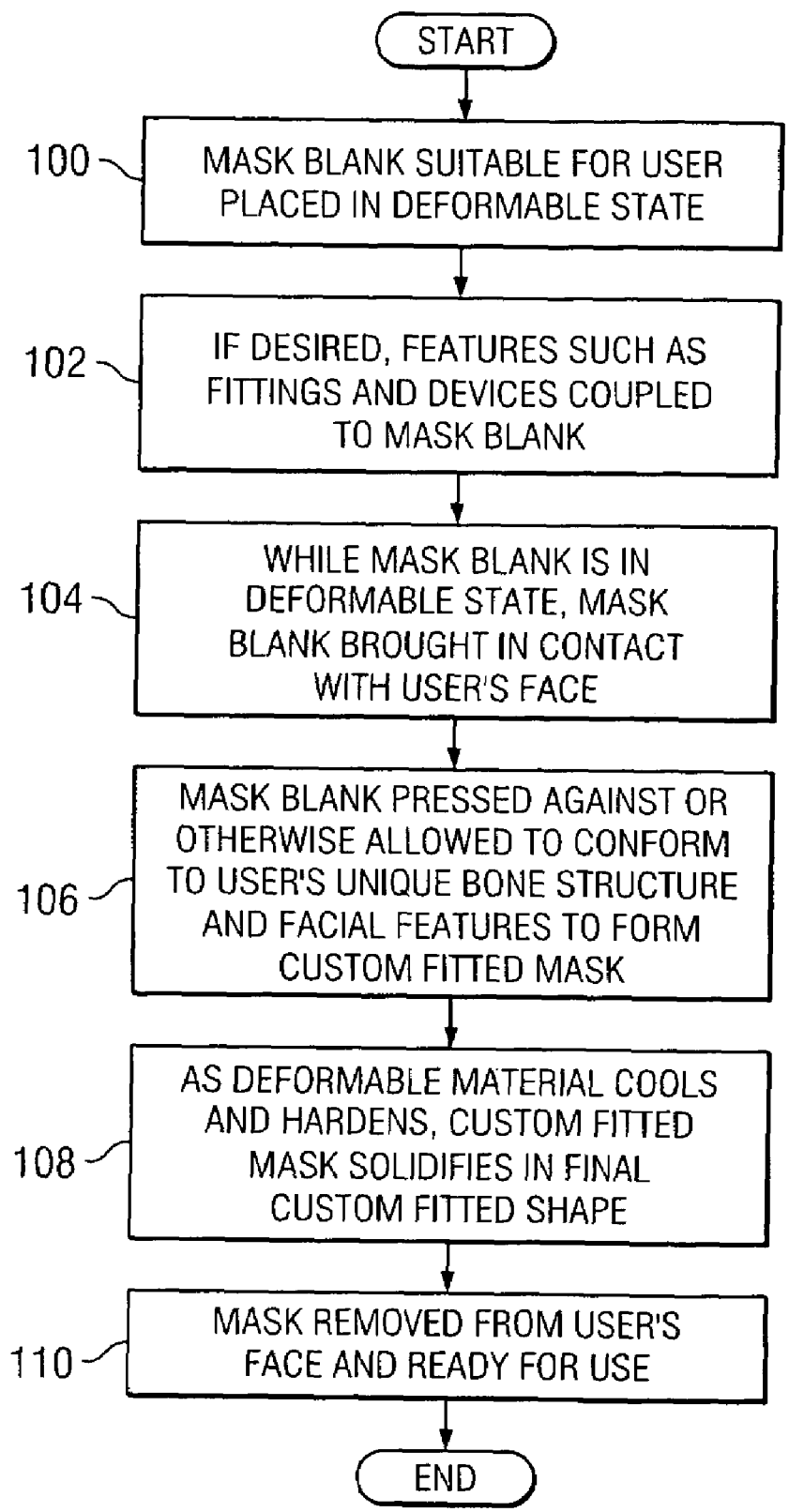
FIG. 7 illustrates an example method of forming a custom fitted mask for a particular user.

FIGS. 6A, 6B, and 6C illustrate example sheets of deformable material 30 for use as mask blanks in constructing the embodiments shown in FIGS. 1, 4A, and 5A respectively.

Although mask 12 is described primarily for use in treating breathing problems such as sleep disordered breathing, the present invention contemplates mask 12 being used or for any other suitable purpose for which a custom fitted mask may be used. As just one example, mask 12 may be used in delivering anesthetics during surgery or another medical procedure.

FIG. 6 illustrates an example method of forming a custom fitted mask 12 for a particular user. The method begins at step 100, a mask blank suitable for the user is placed in a deformable state. At step 102, if desired, features such as fittings 18 and devices 24 may be coupled to the mask blank if such features are not already coupled to the mask blank. At step 104, while the mask blank is in a deformable state, the mask blank is brought in contact with the user's face, including at least a portion of the user's nose surrounding the user's nostrils. At step 106, the mask blank is pressed against or otherwise allowed to conform to the user's unique bone structure and facial features to form mask 12. At step 108, as the deformable material cools and hardens, mask 12 solidifies in its final custom fitted shape. At step 110, mask 12 is removed from the user's face and is ready for use, for example, in treating sleep disordered breathing.

Although the present invention has been described above in connection with several example embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A mask blank for using in forming a custom fitted mask, comprising a thin sheet of deformable material having a perimeter, the perimeter defining a first portion of a generic user' face to include only soft cartilaginous portions of the generic user's nose and portions of the generic user's face on either side of and below the soft cartilaginous portions of the generic user's nose and to exclude hard bony portions of the generic user's nose generally above the soft cartilaginous portions of the generic user's nose;
    wherein the thin sheet of deformable material is adapted to be:
        transitioned from a non-deformable state into a deformable state;
        applied against at least a first portion of a particular user's face surrounding the particular user's nostrils while the mask blank is in the deformable state; and
        deformed against the first portion of the particular user's face to cause the mask blank to conform substantially optimally to the particular user's unique facial features to form the custom fitted mask; and
    wherein:
        the thin sheet of deformable material includes a depression sufficient to accommodate at least a portion of the generic user's nose surrounding the generic user's nostrils;
        the thin sheet of deformable material is substantially flat on either side of and below the depression; and
        the thin sheet of deformable material is adapted to be deformed against at least a first portion of the particular user's face surrounding the user's nostrils.

2. The mask blank of claim 1, further adapted to be:
    applied against at least a second portion of the particular user's face surrounding the particular user's mouth while the mask blank is in the deformable state; and
    deformed against the second portion of the particular user's face to cause the mask blank to conform substantially optimally to the particular user's unique facial features to form the custom fitted mask.

3. The mask blank of claim 2, wherein the mask blank comprises a first portion for applying to the first portion of the particular user's face and a second portion for applying to the second portion of the particular user's face, the first portion of the mask blank adapted to be coupled to the second portion of the mask blank in forming the custom fitted mask.

4. The mask blank of claim 2, further adapted to be:
    applied against at least a third portion of the particular user's face under the user's chin while the mask blank is in the deformable state; and
    deformed against the third portion of the particular user's face to cause the mask blank to conform substantially optimally to the particular user's unique facial features to form the custom fitted mask.

5. The mask blank of claim 3, wherein the mask blank comprises a first portion for applying to the first portion of the particular user's face and a second portion for applying to the second and third portions of the particular user's face, the first portion of the mask blank adapted to be coupled to the second portion of the mask blank in forming the custom fitted mask.

6. The mask blank of claim 1, wherein the mask blank comprises an injection molded mask blank.

7. A mask blank for using in forming a custom fitted mask, comprising:
a thin sheet of deformable material having a perimeter, the perimeter defining a first portion of a generic user's face to include only soft cartilaginous portions of the generic user's nose and portions of the generic user's face on either side of and below the soft cartilaginous portions of the generic user's nose and to exclude hard bony portions of the generic user's nose generally above the soft cartilaginous portions of the generic user's nose;
wherein the thin sheet of deformable material:
includes a depression sufficient to accommodate at least a portion of the generic user's nose surrounding the generic user's nostrils;
is substantially flat on either side of and below the depression; and
is adapted to be:
transitioned from a non-deformable state into a deformable state;
applied against at least a first portion of a particular user's face surrounding the particular user's nostrils while the mask blank is in the deformable state; and
deformed against the first portion of the particular user's face to cause the mask blank to conform substantially optimally to the particular user's unique facial features to form the custom fitted mask; and
holes, one for each of the generic user's nostrils, adapted to receive fittings for coupling the custom fitted mask to an external gas supply system.

8. A mask blank for using in forming a custom fitted mask, comprising:
a thin sheet of deformable material having a perimeter, the perimeter defining a first portion of a generic user's face to include only soft cartilaginous portions of the generic user's nose and portions of the generic user's face on either side of and below the soft cartilaginous portions of the generic user's nose and to exclude hard bony portions of the generic user's nose generally above the soft cartilaginous portions of the generic user's nose;
wherein the thin sheet of deformable material:
includes a depression sufficient to accommodate at least a portion of the generic user's nose surrounding the generic user's nostrils;
is substantially flat on either side of and below the depression; and
is adapted to be:
transitioned from a non-deformable state into a deformable state;
applied against at least a first portion of a particular user's face surrounding the particular user's nostrils while the mask blank is in the deformable state; and
deformed against the first portion of the particular user's face to cause the mask blank to conform substantially optimally to the particular user's unique facial features to form the custom fitted mask; and
holes for receiving devices for coupling the custom fitted mask to one or more straps for securing the custom fitted mask to the particular user's face.

9. A mask blank for using in forming a custom fitted mask, comprising a thin sheet of deformable material having a perimeter, the perimeter defining a first portion of a generic user's face to include only soft cartilaginous portions of the generic user's nose and portions of the generic user's face on either side of and below the soft cartilaginous portions of the generic user's nose and to exclude hard bony portions of the generic user's nose generally above the soft cartilaginous portions of the generic user's nose;
wherein the thin sheet of deformable material:
includes a depression sufficient to accommodate at least a portion of the generic user's nose surrounding the generic user's nostrils;
is substantially flat on either side of and below the depression; and
is adapted to be:
transitioned from a non-deformable state into a deformable state;
applied against at least a first portion of a particular user's face surrounding the particular user's nostrils while the mask blank is in the deformable state; and
deformed against the first portion of the particular user's face to cause the mask blank to conform substantially optimally to the particular user's unique facial features to form the custom fitted mask; and
wherein the deformable material comprises a thermoplastic polymer and the mask blank must be heated to transition the mask blank into the deformable state.

10. The mask blank of claim 9, wherein the thermoplastic polymer comprises a polycaprolactone polymer.

11. The mask blank of claim 9, wherein the custom fitted mask when in use is adapted to cover a portion of the particular user's face surrounding the particular user's nostrils, the portion of the particular user's face comprising only soft cartilaginous portions of the particular user's nose and portions of the particular user's face on either side of and below the soft cartilaginous portions of the particular user's nose but does not cover hard bony portions of the particular user's nose generally above the soft cartilaginous portions of the particular user's nose.

12. The mask blank of claim 9, wherein the custom fitted mask comprises a mask for use in treating sleep disordered breathing.

13. A mask blank for using in forming a custom fitted mask for treating sleep disordered breathing, the mask blank comprising:
a thin sheet of deformable thermoplastic polymer material contoured in the shape of a portion of a generic user's face surrounding the generic user's nostrils, the thin sheet of deformable material comprising:
a perimeter defining the portion of the generic users s face to include only soft cartilaginous portions of the generic user's nose and portions of the generic user's face on either side of and below the soft cartilaginous portions of the generic user's nose and to exclude hard bony portions of the generic user's nose generally above the soft cartilaginous portions of the generic user's nose; and
an interior within the perimeter, the interior configured to overlay only the soft cartilaginous portions of the generic user's nose and portions of the generic user's face on either side of and below the soft cartilaginous portions of the generic user's nose;

the thin sheet of deformable thermoplastic polymer material including a depression sufficient to accommodate at least a portion of the generic user's nose surrounding the generic user's nostrils and being substantially flat on either side of and below the depression;

the thin sheet of deformable thermoplastic polymer material comprising holes, one for each of a particular user's nostrils, adapted to receive fittings for coupling the custom fitted mask to an external gas supply system, the thin sheet of deformable thermoplastic polymer material adapted to be:

heated to transition the mask blank from a non-deformable state into a deformable state;

applied against a portion of the particular user's face surrounding the particular user's nostrils while the mask blank is in the deformable state, such that the interior within the perimeter of the mask blank overlays only soft cartilaginous portions of the particular user's nose and portions of the particular user's face on either side of and below the soft cartilaginous portions of the particular user's nose and does not overlay hard bony portions of the particular user's nose generally above the soft cartilaginous portions of the particular user's nose; and deformed against the portion of the particular user's face to cause the mask blank to conform substantially optimally to the particular user's unique facial features to form the custom fitted mask.

\* \* \* \* \*